United States Patent [19]

Torney et al.

[11] 4,055,466
[45] * Oct. 25, 1977

[54] CULTURE MEDIUM FOR TISSUE CULTURE TECHNIQUES

[75] Inventors: Harry L. Torney; Helen T. Torney, both of Indianapolis, Ind.; Dale E. Bordt, Des Moines, Iowa

[73] Assignee: Johnson & Johnson, New Brunswick, N.J.

[*] Notice: The portion of the term of this patent subsequent to June 3, 1992, has been disclaimed.

[21] Appl. No.: 582,462

[22] Filed: May 30, 1975

Related U.S. Application Data

[63] Continuation of Ser. No. 377,838, July 9, 1973, Pat. No. 3,887,430, which is a continuation of Ser. No. 229,219, Feb. 24, 1972, abandoned, which is a continuation of Ser. No. 58,203, July 24, 1970, abandoned.

[51] Int. Cl.$^2$ .............................................. C12B 3/00
[52] U.S. Cl. ...................................... 195/1.7; 195/1.8
[58] Field of Search .......................................... 195/1.7

[56] References Cited

U.S. PATENT DOCUMENTS

| 3,249,504 | 5/1966 | Cappel et al. | 195/1.7 |
| 3,887,430 | 6/1975 | Torney et al. | 195/1.7 |

OTHER PUBLICATIONS

Johnson et al. - J. Bacteriology, vol. 80, pp. 406–411.

*Primary Examiner*—Sam Rosen
*Attorney, Agent, or Firm*—Salvatore R. Conte; Geoffrey G. Dellenbaugh

[57] ABSTRACT

A chemically defined, protein-free culture medium embodying an anion-exchange resin and a water-soluble lipid source provides means for tissue culture.

3 Claims, No Drawings

CULTURE MEDIUM FOR TISSUE CULTURE TECHNIQUES

CROSS-REFERENCE TO RELATED APPLICATION

This is a continuation of application Ser. No. 377,838 filed July 9, 1973 now U.S. Pat. No. 3,887,430, which is a continuation of Ser. No. 229, 219 filed Feb. 24, 1972, now abandoned which is a continuation of Ser. No. 58,203 filed July 24, 1970, now abandoned.

BACKGROUND OF THE INVENTION

A number of viruses are known to be of economic importance by reason of their role as the causative agent of certain diseases in animals. In the investigation of such viruses, and in development of vaccines and other materials for prophylaxis for such diseases, it has been a common practice to culture living animal cells in vitro. Many viruses, as well as various economically and scientifically significant microorganisms such as bacteria, rickettsiae and pleuropneumonia-like organisms (PPLO) have been made susceptible to laboratory examination by virtue of propagation in tissue culture of living animal cells. For example, many viruses have been isolated from diseased animals, propagated, and modified by attenuation or killed by specialized techniques after propagation by means including tissue culture as a central element. Tissue culture techniques are employed in the production of vaccines, in assay of viruses, in antibody assay, in interferon assay, in virus isolation procedures, in propagation of established virus strains, and a number of other techniques. Widespread use of tissue culture techniques has given economic significance to various cell lines, propagated in vitro for several successive transfers, which are employed in assay procedures, genetic studies, vaccine production and a number of other areas.

Many media for the propagation and maintenance of cells in tissue culture are known. Among these are a number of chemically-defined media, such as medium 199 of Morgan, Morton and Parker, Proc. Soc. Exptl. Biol. & Med. 73:1–8 (1950), Eagle's Basal Medium, Science 122:501–504 (1955), Science, 123:845–847 (1956), J. Biol. Chem. 226:191–206 (1957) and Eagle's Minimum Essential Medium, Science, 130:432–437 (1959) which may also include various balanced salt solutions (BSS) such as Hanks BSS, Earle BSS, Dulbecco Phosphate-buffered saline, Puck Saline F., Puck Saline G and the like. Merchant et al., Handbook of Cell and Organ Culture, Burgess Publishing Co., Minneapolis (1964). Such media materials consist of defined identifiable carbohydrates, minerals, amino acids, vitamins, salts, etc. in definite amounts, thus ensuring the identity of the medium from batch to batch. Other materials employed in tissue culture techniques, usually together with a chemically defined medium or balanced salt solution, include natural extracts and protein hydrolysates such as yeast extract, lactalbumin hydrolysate, Scherer maintenance medium, tryptone, tryptose, peptone, La Ye (lactalbumin hydrolysate-yeast extract) and the like. Such other extract and hydrolysate materials are not chemically defined, and are thus not susceptible of as wide application as are the synthetic chemically defined media. Both the chemically defined media and the natural extract and protein hydrolysate materials can be sterilized by autoclaving prior to use. A third class of material utilized in tissue culture techniques, often as a supplement to a chemically defined medium, are the natural animal protein materials such as albumins, globulins, or animal serum such as human, calf, bovine, lamb, rabbit serum or the like. The natural materials are characteristically neither chemically defined nor chemically pure. They can carry viral, rickettsial, PPLO, bacterial or other biological contaminants, and cannot be sterilized by heat without thermal degradation or inactivation of the desired animal protein. They may also be cytotoxic as respect some tissue, or they may carry undesired viral inhibitors or materials unsuitable for use in vaccine production or assay techniques.

Some of the problems inherent in the use of serum in virus production can be alleviated in many cases. For example, serum-containing growth media employed in growing cells for virus propagation can be replaced with a serum-free medium prior to inoculation with the virus to be propagated. However the replacement of the serum-containing medium typically requires repeated washing of the cells to ensure removal of the serum. The increased handling during the washings increases risks of contamination. Further, elaborate precautions must be taken to minimize the risk of contamination, thus making the multiple washing operation a tedious and expensive procedure. Propagation of the cells in an autoclavable serum-free or protein-free medium would eliminate the need for such washings, as well as elminating the risks and expense incurred in using serum in the growth medium. It would thus be desirable to provide a serum-free medium which can be used in both tissue culture growth and virus propagation.

Further, it is desirable to avoid the use of proteins and the like natural products since such materials are subject to considerable variability from batch to batch. Various autoclavable media for the growth of animal cells and for propagation of viruses have been employed. However, in most cases much more rapid and abundant propagation of cells and of viruses is obtained when such media are supplemented with animal serum or albumin. A chemically defined medium free of animal protein which provides enhanced cell and virus propagation would clearly be desirable.

A serum-free chemically defined medium comprising a buffered aqueous solution of carbohydrates, amino acids, mineral salts and vitamins, a water-soluble lipid source and a basic anion-exchange resin is described by Torney, U.S. patent application Ser. No. 725,517 filed Apr. 30, 1968. The medium is taught to be useful in growing Leptospira organisms.

SUMMARY OF THE INVENTION

In accordance with the present invention there is provided an improved protein-free composition suitable for tissue culture of animal cells, and for production of viruses with excellent yields. The improved composition comprises a conventional chemically-defined culture medium including a buffered aqueous solution of sugars, amino acids, mineral salts and vitamins and further comprises a growth-enhancing amount of water-soluble lipid source and an amount of a basic anion-exchange resin. The invention further comprises methods for employing the improved compositions in tissue culture and in propagation of viruses.

In carrying out the invention the medium may be prepared directly by dissolving together in distilled water each of the required ingredients and adding to the resulting solution the required growth-enhancing amount of ion exchange resin and the water-soluble lipid source. Alternatively in the latter step the lipid source and ion exchange resin may be mixed together separately, with heating if desired, and added together to the solution of other essential ingredients. In practice, it is convenient to supply the essential amino acids, sugars, salts and vitamins primarily in the form of one of the standard chemically defined media such as Medium 199 Eagle's Basal Medium, Eagle's Minimum Essential Medium, or the like.

In preparing the compositions of the invention it is critical and essential to employ a growth-enhancing amount of each of the lipid source and the anion-exchange resin. The exact growth-enhancing amount of lipid source and anion-exchange resin to be employed in a given case is dependent upon such factors as the particular chemically-defined medium employed, the precise lipid source and anion-exchange resin employed, the tissue employed, whether the cells to be grown are primary cells or from a cell line, whether the cells to be grown have been previously propagated in protein-free media, and the like. In a particular case, the optimum amounts of lipid source and anion-exchange resin to be employed can be ascertained by conventional range-finding procedures. Good results are obtained when employing from about 0.5 to about 4 parts by volume of the resin and from about 0.01, to about 0.1 parts by volume of water-soluble lipid source per 100 parts by volume of the finished medium. Excellent results have been obtained with an improved medium containing from about 0.1 to about 2 parts by volume of resin and from about 0.002 to about 0.004 parts by volume of lipid source per 100 parts of a conventional chemically-defined standard medium such as medium 199 or Eagle's Basal Medium. Suitable anion-exchange resins include weakly basic anion-exchange resins and strongly basic anion-exchange resins. Typical weakly basic anion-exchange resins may be prepared in accordance with the teachings of U.S. Pat. Nos. 2,591,574; 2,597,439 and 2,642,417. In such operations a vinyl-aromatic compound such as styrene is copolymerized with a minor proportion of a cross-linking agent such as divinylbenzene to produce a cross-linked polystyrene. The latter is then reacted in accordance with the teachings of the above patents with a halomethylating agent such as chloromethyl methyl ether to produce a halomethylated polystyrene. This halomethylated polymeric product is thereupon reacted with a primary or secondary amine or with a polyamine such as polyalkylenepolyamine to produce the desired weakly basic anion-exchange resin. In preparing a strongly basic anion-exchange resin the halomethylated polymeric product, prepared in the above manner, is reacted with a tertiary amine to introduce a plurality of quaternary ammonium groups on the polymer structrue and thereby produce the desired anion-exchange resin. Commercially available resins may be employed as, for example, the weakly basic anion-exchange resin sold by the Rohm & Haas Company under the trademark Amberlite IR-45 or the strongly basic anion-exchange resins sold by The Dow Chemical Company under the trademarks Dowex 1 and Dowex 2. In general, it is preferred to employ a resin having a high water-holding capacity indicating a relatively low degree of crosslinking, for example, a resin prepared by initially copolymerizing styrene with only about 2 to 4 percent of divinylbenzene. It is further preferred to employ such a resin having a particle size of from about 20 mesh to about 400 mesh.

Any suitable water-soluble lipid source may be employed, such as, for example, sodium oleate or a mixture of sodium oleate and sodium stearate. In a preferred embodiment, however, the lipid requirement of the culture medium is supplied in the form of a polysorbate, that is, a water soluble polyoxyethylene derivative of a sorbitan monoester of a fatty acid. Such polysorbates are available commercially from the Atlas Powder Company under the trademark Tween. Of such polysorbates the polyoxyethylene derivative of sorbitan mono-oleate (polysorbate 80) and particularly the polyoxyethylene derivatives of sorbitan monostearate (polysorbate 60) are preferred.

In employing the medium, conventional tissue culture techniques may be used. The usual precautions to avoid contamination are necessary. Good results have been obtained when the sugar, amino acid, salt and vitamin solution of the medium of the invention, after sterile filtration, is inoculated with living animal cells, the required amounts of resin and lipid source are added, after autoclaving, and the resulting cultures thereafter maintained at a temperature of 28° to 37° C. for a period of time until the desired growth of the tissue is obtained. Inoculation of the resulting cell sheet with virus, addition of fresh medium, harvesting and virus purification and assay are similarly carried out according to conventional techniques.

The growth of cells and formation of a tissue monolayer in the use of the medium of the invention is generally accompanied by growth of cells on particles of the anion-exchange resin, particularly when the inoculated medium is incubated in a stationary culture vessel. In other chemically defined media or in media containing serum, but lacking the resin and lipid source of the present invention, growth of a tissue monolayer is confined to the surfaces of the culture vessel which contact the medium. In the present medium, growth also can take place on the resin particles, which, being insoluble, rapidly settle in the culture vessel, forming a bed or layer of particles on the lower surfaces thereof.

In the case of primary cells, growth typically occurs both on the resin particles as well as on the walls of the culture vessel. When the cells employed are from a cell line which has been previously adapted to grow in a medium containing animal serum or other animal protein, tissue growth has been observed to be on the resin particles to the exclusion of the walls of the culture vessel.

When virus is propagated in tissue culture utilizing the resin and lipid source-containing medium, improved virus titers can be generally obtained as compared either with other chemically-defined media or with media containing animal protein. In addition, significant increases in virus yield have been obtained by employing increased volumes of medium and inoculum. In utilizing such increased volumes of material, three-fold or greater increases in virus titers have been observed with two-fold increases in the volume of medium, and inoculum employed, the concentrations of resin, lipid source, sugars, amino acids, salts, vitamins, initial cell dispersion and virus inoculum being the same. Thus, the present invention provides further improvements in propagation of viruses in addition to that which would result from the improvements in tissue culture resulting from the use of the invention.

In certain cases, typically in tissue culture of cells from a cell line adapted to growth in serum-containing media, it can be desirable to employ an autoclaved extract such as yeast extract or an autoclaved protein hydrolysate in conjunction with the chemically-defined medium of the invention. While the resulting medium is not chemically-defined, it is nevertheless free of unsterilized components such as serum. In accordance with the invention, an autoclaved natural product such as yeast extract, lactalbumin hydrolysate, peptone, peptose, tryptone or tryptose is employed in an amount sufficient to enhance the growth of the cell line cells adapted to grow in serum-containing media in the sterile resin and lipid source-containing medium, and such cells are propagated in such autoclaved, sterile medium for a sufficient number of serial transfers to adapt the cell line cells to the absence of serum. In general, adaptation of the cell line to the absence of serum, as indicated by tissue growth in the sterile, autoclaved medium comparable to growth of cells of the same origin in serum-containing media, is obtained after from 1 to 2 or 3 or 4 passages in the serum-free medium. The cells can then be further adapted to the sterile, chemically-defined medium of the invention by carrying out additional serial transfers with decreasing amounts of autoclaved natural product until good tissue growth is obtained in the absence of the autoclaved natural product. Conventional procedures, such as terminal dilution techniques, can be employed to facilitate adaption of the originally serum-dependent cell line to the chemically-defined medium of the invention.

DESCRIPTION OF PREFERRED EMBODIMENTS

The following examples illustrate the invention but are not to be construed as limiting the same.

Example 1

A Lipid Concentrate is prepared by dissolving polysorbate 60 (Tween 60) in glass-distilled water to give a solution containing 500 milligrams of polysorbate 60 per 100 milliliters of solution.

The Resin Ingredient is similarly prepared in bulk prior to formulation of the medium of the invention by forming a bed of resin in a glass cylinder and washing the resin with the following materials in the order indicated by the numerals below:

| Order of Washing | Wash Material | Number of Bed Volumes of Wash Material Employed |
|---|---|---|
| 1 | Distilled Water | 5 |
| 2 | Aqueous 1 Normal Hydrochloric Acid | 5 |
| 3 | Distilled Water | 5 |
| 4 | Aqueous 1 Normal Sodium Hydroxide | 5 |
| 5 | Distilled Water | 5 |
| 6 | Aqueous 1 Normal Hydrochloric Acid | 5 |
| 7 | Distilled Water | 20 |

The washed resin is then dispersed in aqueous 0.1 Normal sodium chloride solution, between 10 and 50 grans of resin to 100 milliliters of solution. The pH of the dispersion is adjusted to pH 7.0 by the addition of aqueous 1 Normal sodium hydroxide with constant agitation. The resin is sterilized by autoclaving with about five volumes of water. The anion exchange resin employed is a strongly basic anion-exchange resin (Dowex 1) obtained by reacting trimethylamine with a halomethylated polymer in bead form. The halomethylated polymer is prepared by reacting chloromethyl methyl ether in the presence of a zinc chloride catalyst with beads of a copolymer of 98 percent of styrene and 2 percent of divinylbenzene.

Example 2

Medium 199 of Morgan, Morton and Parker, a synthetic nutrient medium, is prepared, sterile filtered, inoculated with primary chick embryo cells at a cell concentration of 630,000 cells per milliliter, and placed in each of four culture vellels A, B, C, D, in the amount of 75 milliliters per vessel. 0.0025 milliliters of lipid source, polysorbate 60 (Tween 60) are added to two such vessels, A and B. The lipid source being added in the form of an autoclaved Lipid Concentrate of Example 1, 0.5 milliliters of the Lipid Concentrate being employed to provide 0.0025 milliliter of lipid source. 0.3 milliliter of anion exchange resin is added to vessels A and C, the resin being previously sterilized by autocalaving. The culture vessels are incubated at a temperature of 35° C. Tissue growth is evaluated over a 7day period, beginning 48 hours after inoculation. Poor growth is observed in vessel D, good growth is observed in both vessels B and C with formation of a good cell sheet on the glass culture vessel surface in contact with the medium, and good growth is observed in vessel A, the growth being poor on the glass but good on the resin particles.

Example 3

The procedure of Example 2 is repeated employing various amounts of the polysorbate 60 lipid source and of the resin, prepared as described in Example 1. 75 milliliters of Medium 199 with 3.75 milliliters of calf serum is employed for comparison. Tissue is incubated at a temperature of 35° C. Beginning 24 hours after incubation, the extent of cell growth is evaluated daily for 7 days. The extent of growth is recorded on a scale from 0, indicating no growth to 4, indicating excellent growth with formation of an extensive cell monolayer. The results are set out in the following table.

| Milliliters of Resin | Milliliters of Polysorbate 60 | Milliliters of Calf Serum | Tissue Growth | |
|---|---|---|---|---|
| | | | On Glass | On Resin |
| 0 | 0 | 0 | 4+ | 0 |
| 0 | 0 | 3.75 | 4+ | 0 |
| 0 | 0.0025 | 0 | 4+ | 0 |
| 0.3 | " | 0 | 4+ | 4 |
| 0.6 | " | 0 | 4+ | 4 |
| 0.9 | " | 0 | 3+ | 4 |
| 1.2 | " | 0 | 3+ | 4 |
| 1.5 | " | 0 | 3+ | 4 |
| 1.8 | " | 0 | 3 | 3 |
| 2.1 | " | 0 | 2+ | 3 |
| 2.4 | " | 0 | 2+ | 2 |

Example 4

Employing procedures similar to those described in the preceding Examples, medium 199, and the polysorbate 60 and resin of Example 1 are employed in the growth of measles virus (live attentiated measles virus, Schwarz strain) in chick embryo tissue culture by the procedure of Schwarz, U.S. Pat. No. 3,133,861. The culture vessels are observed for cell growth, and the virus is harvested by conventional techniques and titered in VERO cells. The amounts of resin, polysorbate 60, calf serum and medium 199 employed in each vessel are set out below in milliliters (ml) together with the results obtained.

| Vessel | Resin | Polysorbate 60 | Calf Serum | Medium 199 | *Tissue Appearance after 7 days Glass | Resin | Yield of Measles Virus in $TCID_{50}$/ 0.2 Milliliters** |
|---|---|---|---|---|---|---|---|
| A | 0 | 0 | 0 | 100 | 4 | None | 1259 |
| B | 0 | 0 | 3.75 | 100 | 4 | None | 316 |
| C | 0.6 | 0.0025 | 0 | 100 | 4 | Good | 1995 |
| D | 1.2 | 0.0050 | 0 | 200 | 4 | Good | 7943 |

*Cells inoculated with measles virus one day after incubation of cells. Cytopathic effects in chick embryo cell sheet indicative of virus replication is observed in vessels C and D about 1–2 days prior to observation of cytopathic effects in vessels A and B.
**Tissue Culture Infecting Dose-50 percent in 0.2 milliliter of harvest liquid as titered in VERO cell culture.

Example 5

The procedure of Example 4 is repeated employing chick embryo tissue culture for determination of virus yield and employing various amounts of medium. The results are set out below.

| Amount of Ingredient in Milliliters per Vessel | | | | Virus Yield in $TCID_{50}$/ |
|---|---|---|---|---|
| Resin | Polysorbate 60 | Calf Serum | Medium 199 | 0.2 Milliliters |
| — | — | — | 100 | 19950 |
| — | — | — | 200 | 19950 |
| — | — | 3.75 | 100 | 50120 |
| — | — | 7.50 | 200 | 50120 |
| 0.6 | 0.0025 | — | 100 | 79430 |
| 1.2 | 0.0050 | — | 200 | 1999500 |

Example 6

Mumps virus (Jones strain) is grown in chick embryo tissue culture using the medium of the invention, with medium 199 with and without added calf serum employed for comparison. In the first such operation, medium 199 containing about $10^6$ cells per milliliter is employed with a mumps virus inoculum of one milliliter of a preparation containing $10^{3.5} TCID_{50}$ live mumps virus. In the second operation, medium 199 containing about $10^6$ cells per milliliter is employed with a mumps virus inoculum of $10^{3.5} TCID_{50}$. The virus yield, as determined by titration in chick embryo tissue culture, is set out below.

| Ingredient in Milliliters | | | | Virus Yield $TCID_{50}$/0.2 Milliliters | |
|---|---|---|---|---|---|
| Resin | Tween 60 | Calf Serum | Medium | Operation I | Operation II |
| — | — | — | 100 | 316,200 | 31,620 |
| — | — | 3.75 | 100 | 79.430 | 7,943 |
| 0.6 | 0.0025 | — | 100 | 50,120 | 794,430 |
| 1.2 | 0.0050 | — | 200 | 3,162,000 | 1,995,000 |

The results obtained in the preceding Examples 1–6 indicate the improvements in both cell and virus yields which can be obtained by the practice of the present invention. Further, such results indicate the outstanding improvements which can be obtained by utilization of the medium of the invention in increased ratios of volume to surface area.

The following Examples illustrate the use of the method and medium of the invention in propagation of cells from a cell line.

Example 7

Cells from the Madin-Darby Bovine Kidney cell line (MDBK) are dispersed in Eagle's medium which has been previously sterilized by filtration. The cell dispersion is aseptically measured into sterile Blake bottles, 150 milliliters of the dispersion being added to each bottle. 7.5 milliliters of fetal lamb serum are added to one of the bottles (A); 1.2 milliliters of resin and 0.002 milliliters of polysorbate 60 (0.4 milliliters of Lipid Concentrate) prepared as described in Example 1 are added to three other Blake bottles, B, C and D, the resin and polysorbate 60 having been sterilized by autoclaving prior to use. In addition, 15 milliliters of an aqueous 5 percent by weight solution of lactalbumin hydrolysate, sterilized by autoclaving, are added to bottle C, and 0.75 grams of autoclaved tryptone are added to bottle D. A fifth bottle, E, is employed as a check, containing only the cell dispersion in Eagle's medium. The bottles are incubated at a temperature of 35° C. for 10 days, after which the extent of tissue growth is evaluated. Tissue growth is found to be very poor in the check bottle E wherein only Eagle's medium has been employed, and excellent cell growth is observed in bottle A, containing added lamb serum. No cell growth is observed on the glass in bottles B, C and D; however, moderate to heavy tissue growth is observed on the resin particles. Tissue growth is rated 2, 4 and 3 in bottles B, C, and D, respectively, employing a rating system from 0 for no growth to 4 for excellent growth.

Example 8

Bottles B and C of Example 7 are incubated for an additional day at which time tissue growth is heavy on the resin particles in both bottles. The cells from these bottles are subcultured into fresh medium identical to that employed in the respective bottle in Example 7. MDBK cells of bottle D are subcultured after 17 days. In the subculturing procedure employed, the supernatant liquid is decanted, leaving the cell sheet and resin in the bottle. Cells are harvested by addition of 15 milliliters of a sterile ATV solution (aqueous trypsin and Versene® EDTA chelating agent), incubation at 35° C. for 15 minutes followed by agitation and decantation of liquid containing released cells. The process is repeated employing 10 milliliters of ATV solution and 10 minutes incubation, after which cells remaining on the resin are removed by rinsing with Eagle's medium. The ATV suspensions and Eagle's medium rinse are combined, filtered through sterile gauze, and centrifuged to separate the cells. The cells are resuspended in fresh Eagle's medium and a cell concentration of about 100,000 cells per milliliter for subculturing in the same procedure employed in Example 7. Excellent cell growth is observed early in the incubation of the third subcultures (fourth passage in the medium B, C or D) with notably increased growth as compared to the original passages of Example 7.

Example 9

In a procedure similar to that employed in Examples 7 and 8, MDBK cells previously grown for several serial passages in media containing serum are dispersed in filtered Eagle's medium for a concentration of about 100,000 cells per milliliter. The dispersion is placed in Blake bottles, 150 milliliters per bottle, and the anion-exchange resin of Example 1 and polysorbate 60, and varying amount of sterile tryptone, tryptose or lactalbumin hydrolysate are added. The bottles are incubated for 14 days before evaluation of tissue growth. The added ingredients and the growth observations are set out below.

| Ingredient in Milliliters | | | Ingredient in Grams | | |
|---|---|---|---|---|---|
| Resin | Polysorbate 80 | Aqueous 5% Lactalbumin Hydrolysate | Tryptone | Tryptose | Tissue Growth* After 14 Days |
| — | — | — | — | — | Very Poor |
| 1.5 | 0.002 | — | 0.75 | — | Very good |
| 1.5 | 0.002 | 5.0 | 0.75 | — | Excellent |
| 1.5 | 0.002 | — | — | 0.75 | Good |

*Tissue growth is observed to be on the resin particles and not on the glass.

It will be apparent to those skilled in the art that the particular mixture of sugars, amino acids, vitamins and minerals employed in the culture medium can be varied considerably without departing from the concept of the present invention provided that the essential components, namely a growth-enhancing amount of a water-soluble lipid source and anion-exchange resin, are incorporated in the medium.

What is claimed is:

1. In a serum-free, protein-free, culture medium composition for the propagation of animal tissue cells in tissue culture, the composition comprising a buffered aqueous solution of sugars, amino acids, mineral salts and vitamins, the improvement wherein the culture medium further comprises a growth-enhancing amount of a strongly basic anion-exchange resin obtained by reacting trimethylamine with a halomethylated polymer prepared by reacting chloromethyl methyl ether in the presence of a zinc chloride catalyst with beads of a copolymer of about 90 percent of styrene and 2 percent of divinylbenzene and a water-soluble lipid source selected from the group consisting of polysorbate 60 and polysorbate 80 in an amount of from about 0.001 to about 0.100 parts by volume of lipid source per 100 parts by volume of medium.

2. A composition in accordance with claim 1 wherein the lipid source is polysorbate 60.

3. A composition in accordance with claim 1 wherein the lipid source is polysorbate 80.

* * * * *

UNITED STATES PATENT AND TRADEMARK OFFICE
CERTIFICATE OF CORRECTION

PATENT NO. : 4,055,466
DATED : October 25, 1977
INVENTOR(S) : Harry L. Torney et al It is certified that error appears in the above-identified patent and that said Letters Patent are hereby corrected as shown below:

In Column 6, line 2, "grans" should read --- grams ---.

In Column 7, line 64, "Examples 1-6" should read --- Examples 2-6 ---.

Signed and Sealed this

Thirteenth Day of June 1978

[SEAL]

Attest:

RUTH C. MASON
Attesting Officer

DONALD W. BANNER
Commissioner of Patents and Trademarks